United States Patent
Imbert et al.

(10) Patent No.: US 6,610,725 B1
(45) Date of Patent: Aug. 26, 2003

(54) FLUORINATED IMIDAZOLINE BENZODIOXANE, PREPARATION AND THERAPEUTIC USES THEREOF

(75) Inventors: Thierry Imbert, Viviers les Montagnes (FR); Patrice Mayer, Castres (FR); Marc Marien, Castres (FR); Peters Pauwels, Lautrec (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 10/019,614

(22) PCT Filed: Jun. 29, 2000

(86) PCT No.: PCT/FR00/01825

§ 371 (c)(1), (2), (4) Date: May 7, 2002

(87) PCT Pub. No.: WO01/00619

PCT Pub. Date: Jan. 4, 2001

(30) Foreign Application Priority Data

Jun. 29, 1999 (FR) .............................. 99 08302

(51) Int. Cl.⁷ .................. C07D 405/04; A61K 31/4178
(52) U.S. Cl. ..................................... 514/402; 548/311.7
(58) Field of Search ........................ 548/311.7; 514/402

(56) References Cited

FOREIGN PATENT DOCUMENTS

EP          0 092 328       * 10/1983

* cited by examiner

Primary Examiner—Joseph K. McKane
Assistant Examiner—Rebecca Anderson
(74) Attorney, Agent, or Firm—Dechert

(57) ABSTRACT

The present invention relates to novel fluorinated benzodioxane imidazoline derivatives, to their preparation and to their therapeutic applications.

The invention is directed more particularly toward the compounds corresponding to the structure of general formula 1:

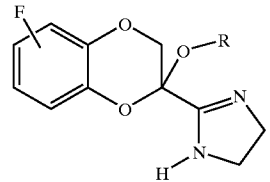

Formula 1 in which:

R represents a linear, branched or cyclized alkyl or alkenyl group containing 1 to 7 carbon atoms, or a benzyl group, and the fluorine atom can occupy position 5, 6, 7 or 8, in their racemic form and their dextrorotatory and levorotatory pure enantiomeric forms, and also the addition salts thereof.

19 Claims, No Drawings

FLUORINATED IMIDAZOLINE BENZODIOXANE, PREPARATION AND THERAPEUTIC USES THEREOF

This is a 371 of PCT/FR00/01835, filed Jun. 29, 2003.

The present invention relates to novel fluorinated benzodioxane imidazoline derivatives corresponding to formula 1.

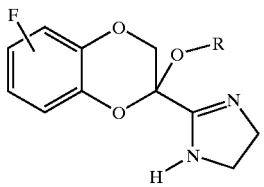

Formula 1 in which:
R represents a linear, branched or cyclized alkyl or alkenyl group containing 1 to 7 carbon atoms, or a benzyl group,
the fluorine atom on the homocycle can occupy position 5, 6, 7 or 8.

The invention relates to the racemic and enantiomerically pure forms, to the salified forms thereof and also to the process for preparing them.

The invention also relates to the use of these compositions as medicinal products, and also to the preparation of a medicinal product used as an $\alpha_2$-adrenergic receptor antagonist and intended in this respect to treat neurodegenerative diseases, and also their progression.

Advantageously, the radical R is a methyl group, an ethyl group, an n-propyl group, an isopropyl group, an isobutyl group, a cyclopropylmethyl group, an allyl group or a benzyl group.

Preferably, the fluorine atom occupies position 5.

It has been shown (Mavridis, Neuroscience (1991), 41, 507) that the locus coeruleus plays a predominant role in the recovery of dopaminergic functions altered by administration of MPTP to monkeys. Its destruction brings about a reduction in recovery. Moreover, compounds with $\alpha_2$-antagonist action are shown as reducing Parkinson's symptoms in monkeys (Colpaert, Brain Res. Bull., 26, 627, 1991) or in rats (Colpaert, Neuropharmacology, 26, 1431, 1987) by elevating the release of dopamine (Marien, M., Colpaert, F. Effect of (+)-efaroxan on mouse striatal dopamine metabolism in vivo. DOPAMINE 94-Satellite Meeting of the XIIth Int. Congr. Pharmacology, Quebec City, Canada, Jul. 20–24, 1994).

Furthermore, an $\alpha_2$-antagonist, idazoxan, is shown as having beneficial action on the deleterious effects of cerebral ischemia (Gustafson, Exp. Brain Res., 86, 555, 1991 et J. Cereb. Blood Flow Metab., 1990, 10, 885) and also in progressive supranuclear paralysis and neurodegenerative disease (Ghika, Neurology, 41, 986, 1991). It has also been shown that compounds with $\alpha_2$-antagonist activity induce an increase in the release of acetylcholine in the prefrontal cortex (Tellez, J.Neurochem. (1997), 68, 778).

Thus, a substance activating the noradrenergic system may have the property of opposing the progression of the degeneration of the involved neurons, by reactivating the various cerebral localization systems, whether they are dopaminergic or cholinergic, or whether this involves the release of growth factors (Fawcett et al. J. Neurosci. (1998), 18, 2808–2821). These compounds are thus useful in cases of neurodegenerative diseases of the type such as Parkinson's disease or Alzheimer's disease and their progression, Huntington's chorea, amyotrophic lateral sclerosis, Creutzfeld-Jacob disease, progressive supranuclear paralysis, cognitive and memory disorders, attention deficit and vigilance deficit in the elderly, and also the progression or evolution of these diseases or disorders. Ischemic and post-ischemic cerebral disorders, cerebrovascular accidents and consequences thereof, depression, narcolepsy and male sexual dysfunctions are also concerned, as are disorders associated with acquired immunodeficiency syndrome.

It is known that benzodioxane derivatives such as idazoxan: 2-(1,4-benzodioxan-2-yl)-2-imidazoline, or alkoxy idazoxan: 2-(2-alkoxy-1,4-benzodioxan-2-yl)-2-imidazoline, have $\alpha_2$-antagonist properties (J. Med. Chem. (1983), 26, 823; J. Med. Chem. (1985), 28, 1054). These compounds have been patented in GB 2 068 376 for idazoxan and in EP 92328 for alkoxy-idazoxans.

It has been shown in these publications that a large number of idazoxan derivatives have been synthesized and tested for their agonist or antagonist action on the $\alpha_1$ or $\alpha_2$ receptors, inter alia, halogenated derivatives, substituted on the aromatic nucleus, have all been found to be less active than or inactive relative to their unsubstituted idazoxan analog (in particular the 6/7-fluoro, chloro or bromo derivative, 5,8-dichloro or 8-chloro derivative). Moreover, the 2-methoxy idazoxan derivative substituted in 6,7 with two methoxy groups showed only extremely marginal activity as an $\alpha_2$-presynaptic antagonist.

The compounds of the present invention differ from the known compounds in that they have a fluorine atom in position 5, 6, 7 or 8 of the aromatic nucleus. They have the property of being powerful $\alpha_2$-adrenergic receptor antagonists.

It has been found, remarkably, that the presence of this fluorine atom in these positions gives these molecules particularly advantageous properties when compared with their nonfluorinated analog.

The pharmacological properties of the products of the present invention have been studied, inter alia, in comparison with those of 2-methoxy idazoxan (RX 821002) and 2-ethoxy idazoxan (RX 811059), which are structurally related compounds that are derivatives not substituted on the aromatic nucleus.

Specifically, we show, in vivo, the superiority of the pharmacological properties of the products of the present invention in the test of memory deficit induced with scopolamine, of the antagonism of the hypothermia induced with guanabenz, an $\alpha_2$-agonist substance, and on the level, in the cortex, of normetanephrine, a metabolite and selective marker for the release of noradrenalin.

Test of the memory deficit induced with scopolamine:

In accordance with the cholinergic hypothesis of the phenomena of learning and memory, scopolamine has amnesiant properties in animals and man. Its administration to a healthy person induces certain amnesia symptoms similar to those observed in Alzheimer's disease. It has been proposed that the scopolamine be used as an experimental pharmacological model of this pathology. The similarities between the memory deficits of Alzheimer's disease and those induced with scopolamine in rats have been published (P. Chopin et M. Briley, The effects of raubasine and dihydroergocristine on an agerelated deficit in passive avoidance learning in rats, J.Pharm.Pharmacol. 42, 375–376, 1990). Scopolamine reduces the capacity for acquisition, memorization and recall in a test of passive avoidance in rats. This involves measuring the reticence, after learning, that the animal has in entering a dark compartment, where it receives a mild electric shock. The administration of scopolamine suppresses this reticence, and the test compounds oppose the effect of scopolamine.

The comparison of the products of the present invention is made with the known compound RX 821002, dextrorotatory enantiomer. The experimental protocol is that published by P. Chopin and M. Briley (Effects of four non-cholinergic cognitive enhancers in comparison with tacrine and galanthamine on scopolamine-induced amnesia in rats: Psychopharmacology, 106, 26–30, 1992).

The results are given in the following table:

| Compounds Active doses over the range from 0.04 to 2.5 mg/kg. | MEMORY DEFICIT INDUCED WITH SCOPOLAMINE Increase in the time taken to enter the dark compartment by the treated animals, relative to those receiving scopolamine alone. (% amplitude of the effect) |
|---|---|
| (+) RX 821002 | non-significant |
| Dextrorotatory compound of Example 1 | 201% |
| Dextrorotatory compound of Example 2 | 198% |
| Tacrine | 191% |
| Donepezil | 67% |

The compounds of the present invention show appreciable activity over a wide range of doses, in contrast with (+) RX 821002, which is not significantly active. The amplitude of its effect is at least as large as that of tacrine, and more active than that of donepezil, reference compounds used therapeutically for Alzheimer's disease.

The value and the appreciable difference of the products of the invention is thus shown.

Inhibition of the hypothermia induced with Guanabenz:

The assessment of the biological activity of the compounds of the invention is also carried out in vivo by studying the inhibition of the hypothermia induced with a central $\alpha_2$-agonist such as guanabenz according to the protocol of S. C. Dilsaver, Pharmacol. Biochem. Behav., 45, 247, 1993.

This test demonstrates the antagonist effect of the $\alpha_2$-adrenergic receptors, in vivo, of the compounds of the invention, and also their activity at the central level. The inhibitory capacities are expressed as the $ED_{50}$ which represent the doses producing a significant inhibition of the hypothermia induced with guanabenz on the one hand, and a normalization, that is to say a return to the normal temperature for the animal, before injection of guanabenz on the other hand. These values are obtained using the method of J. T. Litchfield and F. Wilcoxon (J. Pharmacol. Exp. Ther., 96, 99, 1949). The comparison is made between the 2-methoxy compounds, fluorinated in position 5 (dextrorotatory compound of Example 1) and nonfluorinated: (+) RX 821002, and between the 2-ethoxy, fluorinated in position 5 (dextrorotatory compound of Example 2) and nonfluorinated: (+) RX 811059.

|  | (+) RX 821002 | Dextrorotatory compound of Example 1 |
|---|---|---|
| Range of active doses (i.p) | 0.01–10 0.01 | 0.0025–40 0.003 |
| Inhibition (mg/kg) $ED_{50}$ (mg/kg) |  |  |
| Normalization (mg/kg) $ED_{50}$ (mg/kg) | 0.04–2.5 0.05 | 0.0025–10 0.02 |
| Range of active doses (per os) normalization (mg/kg) $ED_{50}$ (mg/kg) | 0.16–10 0.56 | 0.04–40 0.22 |

|  | (+) RX 811059 | Dextrorotatory compound of Example 2 |
|---|---|---|
| Range of active doses (i.p) | 0.04–10 0.08 | 0.0025–40 0.02 |
| Inhibition (mg/kg) $ED_{50}$ (mg/kg) |  |  |
| Normalization (mg/kg) $ED_{50}$ (mg/kg) | 0.16–10 0.32 | 0.01–10 0.16 |

The greater power of action of the compounds of the invention compared with their analogs (+) RX 821002 and (+) RX 811059 is thus seen. The amplitude of the action is also demonstrated by the determination of the doses inducing the inhibition of hypothermia in 100% of the animals, on 6 doses (each dose separated by a factor of 4) for the dextrorotatory compound of Example 1 against 2 doses for (+) RX 821002. Similarly, the dextrorotatory compound of Example 1 normalizes the hypothermia in 100% of the animals on 3 doses, whereas (+) RX 821002 does not, it does so on only 80% of the animals and at only 2 doses.

|  | (+) RX 821002 | Dextrorotatory compound of Example 1 |
|---|---|---|
| Doses inhibiting the hypothermia in 100% of the animals | 0.16 and 2.5 mg/kg | 0.01–0.04–0.16–0.63–2.5–10 mg/kg |
| Doses normalizing the hypothermia in 100% of the animals | none | 0.16–0.63–2.5 mg/kg |

It is thus seen that the products of the invention have a very broad range of active doses, and are thus better $\alpha_2$-adrenergic antagonists.

Release of noradrenalin:

The level of normetanephrine, a noradrenalin metabolite, in the cerebral tissues is used as a measurement of the release of noradrenalin. Wood, P. L. and coll. Pharmacological Rev. 40, 163–187, (1988), and J. Neurochem. 48, 574–579, (1987)). The formation of normetanephrine, by the action of catechol O-methyltransferase takes place on the outside of the noradrenergic neurones and its measurement takes account of variations in the release of noradrenalin. This measurement is performed in the frontal cortex, a region innervated mainly by the locus coeruleus.

The test compound is administered intraperitoneally to the mice, which are sacrificed after 60 minutes by irradiation with microwaves (to avoid any artefactual changes in the metabolite levels). After dissection, normetanephrine is assayed by HPLC on the cortical tissue extracts. At doses of 0.01 to 2.5 mg/kg, the assayed normetanephrine represents a level from 125 to 150% higher with the compound of Example 1, relative to (+) RX 821002, under the same conditions. This shows the greater efficacy of this compound compared with (+) RX 821002 for the release of noradrenalin.

Binding to the $\alpha_2$-adrenergic receptors in vitro:

It was also confirmed that the compounds of the invention have affinity for the human $\alpha_2$-adrenergic receptors, at the nanomolar level on the basis of tests of binding to the subtypes of these receptors, using tritiated 2-methoxy-idazoxan, [$^3$H] RX821002, as radioactive ligand (J. C. Devedjian and coll. Eur.J.Pharmacol. (1994), 252, 43–49).

The in vivo tests show the advantage which may be afforded by substitution with a fluorine atom on the aromatic nucleus relative to the compound devoid of this substitution.

Since the compounds of the present invention contain an asymmetric carbon, they are in a dextrorotatory form and a levorotatory form. The present invention thus relates also to the enantiomerically pure compounds, to the addition salts thereof and also to pharmaceutical compositions comprising at least one compound of formula 1 and a suitable excipient. The pharmaceutical compositions may be presented in a suitable manner, for oral, injectable or parenteral administration, in the form of wafer capsules, gel capsules, tablets or injectable preparations, at a daily dose of from 0,1 to 200 mg.

The compounds of the present invention may be prepared from 3-fluorocatechol, (described in J.Amer.Chem.Soc. 77, 5314–5317, 1955) by coupling with 2,3-dibromopropionamide in acetonitrile in the presence of $K_2CO_3$ to give the 2 regioisomers 5- and 8-fluoro-1,4-benzodioxane-2-carboxamide. Several recrystallizations make it possible to isolate the 5-fluoro derivative in pure form, at the expense of the 8-fluoro derivative which is more soluble under these conditions. The amide function in position 2 of the benzodioxane is dehydrated into nitrile. This nitrile is then brominated by the action of NBS to give the bromonitrile, which is subjected to the action of a sodium alkoxide such as sodium methoxide in methanol, to form the intermediate imidate which reacts in situ with ethylenediamine to form the desired α-methoxyimidazoline derivative. In a similar manner, the various alkoxy derivatives in position 2 are obtained by treating the preceding bromonitrile derivative by treatment with a corresponding alkali metal alkoxide.

The 2 enantiomers may be separated in several ways: either by diastereoselective crystallization with a chiral acid which may be tartaric acid or derivatives thereof such as dibenzoyltartaric acid, or by chromatographic separation, preparative HPLC, on a chiral phase, giving the dextrorotatory isomer and the levorotatory isomer, the hydrochloride of which may be obtained in crystalline form by the usual methods.

The 6- and 7-fluoro derivatives on the aromatic ring are obtained from (6- or 7-fluoro-2,3-dihydro-benzo[1,4]dioxin-2-yl)methanol, described in J. Med. Chem. (1987), 30, 814. These methanol derivatives are oxidized to acid and then amidated and dehydrated to nitrile according to the processes described in J. Med. Chem. (1983), 26, 823, or J. Med. Chem. (1985), 28, 1054, and then treated as indicated above.

The procedures for the various stages of the synthesis illustrate the invention:

EXAMPLE 1

2-(5-Fluoro-2-methoxy-1,4-benzodioxan-2-yl)-2-imidazoline

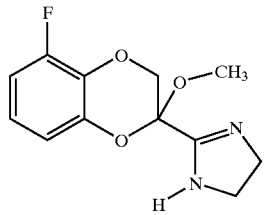

Stage 1: 5-Fluoro-1,4-benzodioxane-2-carboxamide.

A solution containing 50 g of 3-fluorocatechol (391 mmol), 99.3 g of 2,3-dibromopropionamide (430 mmol, 1.1 eq.) and 108.1 g of ground potassium carbonate (782 mmol, 2 eq.) in 400 ml of acetonitrile is heated at 60° C. for 16 hours. The reaction mixture is filtered and the filtrate is then evaporated to dryness. 70.5 g of a pale yellow solid are obtained (92% yield; 1/1 mixture of the two regioisomers). Successive recrystallizations from hot ethanol give 16.7 g of pure 5-fluoro-1,4-benzodioxane-2-carboxamide (22% yield).

Melting point: 167° C. $^1$H NMR (400 MHz, CDCl$_3$) :6.86–6.71 (m, 3H, aromatics); 6.52 (broad s, 1H, NH); 6.11 (broad s, 1H, NH); 4.72 (dd, J=2.4 and 7.2 Hz, 1H, H2); 4.62 (dd, J=2.4 and 11.6 Hz, 1H, H3A); 4.23 (dd, J=7.2 and 11.6 Hz, 1H, H3B).

Stage 2: 5-Fluoro-1,4-benzodioxane-2-carbonitrile 13.7 ml of pyridine (169 mmol, 2 eq.) are added to a suspension of 16.7 g of amide from Stage 1 (84.5 mmol) in 180 ml of dioxane at 0° C., followed, 10 minutes later, by dropwise addition of 13.1 ml of trifluoroacetic anhydride (19.5 g; 93 mmol, 1.1 eq.). The reaction mixture is kept cold for 1 hour and is then stirred at room temperature for 16 hours. The solution is taken up in Et$_2$O/1N HCl. The organic phase is washed with 1N NaOH, dried over MgSO$_4$, filtered and then evaporated to dryness. 16.8 g of a pale yellow oil are obtained (quantitative yield).

$^1$H NMR (400 MHz, CDCl$_3$): 6.90–6.73 (m, 3H, aromatics); 5.15 (dd, J=3.6 and 2.4 Hz, 1H, H2); 4.50 (dd, J=11.6 and 3.6 Hz, 1H, H3A); 4.41 (dd, J=11.6 and 2.4 Hz, 1H, H3B).

Stage 3: 5-Fluoro-2-bromo-1,4-benzodioxane-2-carbonitrile

A solution containing 6.44 g of the nitrile obtained in Stage 2 (36 mmol), 6.40 g of NBS (36 mmol, 1 eq.), and 100 mg of benzoyl peroxide in 200 ml of CCl$_4$ is heated at 70° C. for 48 hours. The mixture is allowed to cool to room temperature. The reaction mixture is then filtered. The solid is washed with CCl$_4$ and the mother liquors are evaporated to dryness. 9.3 g of an orange-yellow oil are isolated (quantitative yield).

$^1$H NMR (400 MHz, CDCl$_3$): 6.93 (m, 2H, aromatics); 6.81 (m, 1H, aromatic); 4.62 (d, J=11.6 Hz, 1H, H3A); 4.48 (d, J=11.6 Hz, 1H, H3B).

Stage 4: 2-(5-Fluoro-2-methoxy-1,4-benzodioxan-2-yl)-2-imidazoline

A solution containing 7 g of 2-bromo-5-fluoro-1,4-benzodioxane-2-carbonitrile (27.1 mmol) and 220 mg of sodium methoxide (4 mmol, 0.15 eq.) in 150 ml of methanol are stirred at room temperature for % hour. 2 ml of ethylenediamine (1.79 g, 29.8 mmol, 1.1 eq.) are then added, followed by 11.3 ml of a 3N HCl/iPrOH solution (34 mmol, 1.25 eq.). The reaction mixture is stirred at room temperature for 16 hours and then taken up in a 1N NaOH/CH$_2$Cl$_2$ mixture. The organic phase is dried over MgSO$_4$, filtered and then evaporated to dryness. The crude product is purified by chromatography on silica under pressure (96/4 CH$_2$Cl$_2$/MeOH). 3.9 g of pure product are obtained (57% yield).

Melting point: 134° C. $^1$H NMR (400 MHz, CDCl$_3$): 6.86–6.74 (m, 3H, aromatics) 5.14 (broad s, 1H, NH); 4.57 (d, J=11.2 Hz, 1H, H3A); 4.00 (d, J=11.2 Hz, 1H, H3B); 3.75 (very broad multiplet, 4H, imidazoline); 3.39 (s, 3H, OCH$_3$).

The hydrochloride is obtained by dissolving 500 mg of base in ether, followed by addition of 661 ml of a 3N HCl/iPrOH solution. The solid formed is filtered off, washed with ether and then dried under vacuum. 480 mg of salt are obtained.

Melting point >260° C. Elemental analysis: Theoretical: C(49.40) H(4.89) N(9.70); Experimental: C(49.42) H(4.91) N(9.61).

The racemic compound in base form (2 g) is chromatographed by successive injections of an amount of from 500 to 800 mg, onto a Prochrom preparative HPLC column of diameter 50 mm (Chiralpack AD), eluting with an 85/15/0.001 hexane/isopropanol/diethylamine mixture. With a flow rate of 100 ml/min, the dextrorotatory and levorotatory enantiomers of the example are successively isolated. The hydrochlorides of the enantiomers are precipitated from ether by adding a stoichiometric amount of ethanol saturated with hydrogen chloride gas.

In particular:

(+) enantiomer:

$[\alpha_D]^{23°}$=+90.80 (c=0.58, MeOH).

Melting point: sublimation from 230° C.

Elemental analysis (C$_{12}$H$_{13}$N$_2$O$_3$F, HCl):

Theoretical: C(49.92) H(4.89) N(9.70);

Experimental: C(49.94) H(4.77) N(9.57).

(−)enantiomer:

$[\alpha_D]^{23°}$=−93.90 (c=0.43, MeOH).

Melting point: sublimation from 230° C.

Elemental analysis (C$_{12}$H$_{13}$N$_2$O$_3$F, HCl):

Theoretical: C(49.92) H(4.89) N(9.70);

Experimental: C(49.89) H(4.83) N(9.61).

EXAMPLE 2

2-(5-Fluoro-2-ethoxy-1,4-benzodioxan-2-yl)-2-imidazoline.

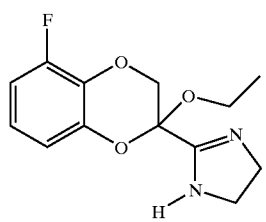

115 mg of sodium are dissolved in 200 ml of ethanol, 8.52 g of 2-bromo-5-fluoro-1,4-benzodioxane-2-carbonitrile (33 mmol), obtained from Stage 3 of Example 1, are then added and the mixture is stirred at room temperature for ¾ hour. 2.43 ml of ethylenediamine (2.18 g; 36.3 mmol; 1.1 mol. eq.) are then added, followed by 13.8 ml of a 3N HCl/iPrOH solution (41.3 mmol, 1.25 mol. eq.). The reaction mixture is stirred at room temperature for 16 hours and then taken up in a iN NaOH/CH$_2$Cl$_2$ mixture. The organic phase is dried over MgSO$_4$, filtered and then evaporated to dryness. The crude product is purified by chromatography on silica under pressure (96/4 CH$_2$Cl$_2$/MeOH). 4.17 g of pure product are obtained (48% yield).

$^1$H NMR (400 MHz, CDCl$_3$): 6.80 (m, 3H, aromatics); 5.14 (broad s, 1H, NH); 4.53 (d, J=11.2 Hz, 1H, H3A); 4.10 (d, J=11.2 Hz, 1H, H3B); 3.97–3.45 very broad multiplet, 4H, imidazoline); 3.70 (m, 2H, OCH$_2$); 1.12 (t, J=7.2 Hz, 3H, CH$_3$).

The two enantiomers are separated by chiral HPLC (Chiralpack AD column; 96/4/0.1 hexane/iPrOH/diethylamine; 100 ml/min; 230 nm).

The hydrochlorides are obtained by dissolving the base in ether, followed by addition of a 3N HCl/iPrOH solution. The solid formed is filtered off, washed with ether and then dried under vacuum.

(+) enantiomer:

$[\alpha_D]^{24}$ (c=0.380; MeOH)=+80.9°.

Melting point >260° C.

Elemental analysis (C$_{13}$H$_{15}$N$_2$O$_3$F, HCl):

Theoretical: C(51.58) H(5.33) N(9.25);

Experimental: C(51.24) H(5.36) N(8.94).

(−) enantiomer:

$[\alpha_D]^{24}$ (c=0.380; MeOH)=−77.6°.

Melting point >260° C.

Elemental analysis (C$_{13}$H$_{15}$N$_2$O$_3$F, HCl):

Theoretical: C(51.58) H(5.33) N(9.25);

Experimental: C(51.80) H(5.39) N(9.02).

The following compounds are obtained according to the same procedures as those described above:

EXAMPLE 3

2-(5-Fluoro-2-propoxy-1,4-benzodioxan-2-yl)-imidazoline Hydrochloride

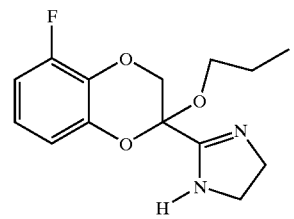

$^1$H NMR (400 MHz, DMSO d6): 11.02 (s, 2H, NH, HCl); 6.99 (m, 2H, aromatics); 6.92 (m, 1H, aromatic); 4.63 (d, J=11.5 Hz, 1H, H3A); 4.23 (d, J=11.5 Hz, 1H, H3B); 3.99 (s, 4H, imidazoline); 3.55 (m, 2H, OCH$_2$); 1.44 (m, 2H, OCH$_2$CH$_2$); 1.12 (t, J=7.2 Hz, 3H, CH$_3$).

Melting point: 206° C. Elemental analysis (C$_{14}$H$_{17}$N$_2$O$_3$F, HCl): Theoretical: C(53.09) H(5.73) N(8.84); Experimental: C(52.29) H(5.82) N(8.63).

EXAMPLE 4

2-(5-Fluoro-2-isopropoxy-1,4-benzodioxan-2-yl)-imidazoline Hydrochloride

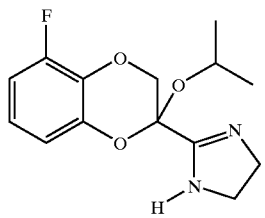

$^1$H NMR (400 MHz, DMSO d6): 10.99 (s, 2H, NH, HCl); 6.99 (m, 2H, aromatics); 6.90 (m, 1H, aromatic); 4.59 (d, J=11.6 Hz, 1H, H3A); 4.18 ((d, J=11.6 Hz, 1H, H3B); 4.08 (m, 1H, OCH); 3.99 (s, 4H, imidazoline ); 1.18 (d, J=6 Hz, 3H, CH$_3$); 0.96 (d, J=6 Hz, 3H, CH$_3$).

Elemental analysis (C$_{14}$H$_{17}$N$_2$O$_3$F, HCl, ½ H$_2$O): Theoretical: C(51.55) H(5.82) N(8.30); Experimental: C(51.62) H(5.88) N(8.60).

EXAMPLE 5

2-(5-Fluoro-2-isobutoxy-1,4-benzodioxan-2-yl)-imidazoline Hydrochloride

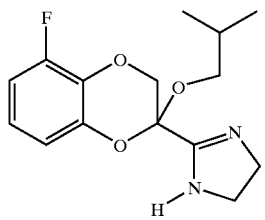

$^1$H NMR (400 MHz, DMSO d6): 10.79 (s, 2H, NH, HCl); 6.97 m, 2H, aromatics); 6.90 (m, 1H, aromatic); 4.61 (d, J=11.4 Hz, 1H, H3A); 4.22 (d, J=11.4 Hz, 1H, H3B); 3.97 (s, 4H, imidazoline); 3.37 (m, 2H, OCH$_2$); 1.70 (m, 1H, CH); 0.75 (d, J=6.8 Hz, 3H, CH$_3$); 0.65 (d, J=6.8 Hz, 3H, CH$_3$).

Melting point: 206° C. Elemental analysis (C$_{15}$H$_{19}$N$_2$O$_3$F, HCl): Theoretical: C(54.47) H(6.09) N(8.47); Experimental: C(53.83) H(6.36) N(8.27).

EXAMPLE 6

2-(5-Fluoro-2-cyclopropylmethyloxy-1,4-benzodioxan-2-yl)-imidazoline Hydrochloride

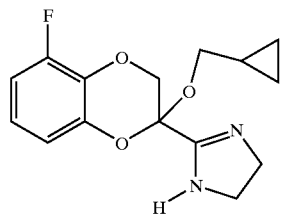

$^1$H NMR (400 MHz, DMSO d6): 10.98 (s, 2H, NH, HCl); 6.99 (m, 2H, aromatics); 6.90 (m, 1H, aromatic); 4.61 (d, J=11, 5 Hz, 1H, H3A); 4.22 (d, J=11, 5 Hz, 1H, H3B); 3.98 (s, 4H, imidazolin); 3.44 (m, 2H, OCH$_2$); 0.93(m, 1H, CH); 0.42 (m, 2H, cyclopropyl); 0.18 (m, 1H, cyclopropyl); 0.00 (m, 1H, cyclopropyl).

Elemental analysis (C$_{15}$H$_{17}$N$_2$O$_3$F, HCl): Theoretical: C(54.80) H(5.52) N(8.52); Experimental: C(54.09) H(5.23) N(8.33).

EXAMPLE 7

2-(5-Fluoro-2-allyloxy-1,4-benzodioxan-2-yl)-imidazoline Hydrochloride

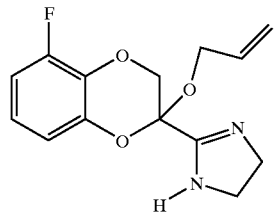

$^1$H NMR (400 MHz, DMSO d6): 11.10 (s, 2H, NH, HCl); 6.99 (m, 2H, aromatics); 6.92 (m, 1H, aromatic); 5.78 (m, 1H, CH=CH$_2$); 5.25 (d, J=17.2 Hz, 1H, CH=CH$_2$); 5.13 (d, J=10.4 Hz, 1H, CH=CH$_2$) 4.68 (d, J=11.6 Hz, 1H, H3A); 4.26 (d, J=11.6 Hz, 1H, H3B); 4.07 (m, 2H, OCH$_2$); 3.98 (s, 4H, imidazoline).

Melting point: 214° C. Elemental analysis (C$_{14}$H$_{15}$N$_2$O$_3$F, HCl): Theoretical: C(53.43) H(5.12) N(8.90); Experimental: C(52.86) H(5.23) N(8.81).

EXAMPLE 8

2-(5-Fluoro-2-benzyloxy-1,4-benzodioxan-2-yl)-imidazoline Hydrochloride

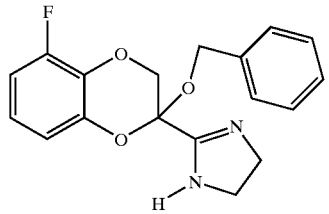

$^1$H NMR (400 MHz, DMSO d6): 11.15 (s, 2H, NH, HCl); 7.30 (m, 3H, aromatics); 7.23 (m, 2H, aromatics); 6.99 (m, 2H, aromatics); 6.91 (m, 1H, aromatic); 4.70 (m, 3H, H3A and PhCH$_2$); 4.29 (d, J=11.6 Hz, 1H, H3B); 3.96 (s, 4H, imidazoline).

Melting point: 218° C. Elemental analysis (C$_{18}$H$_{17}$N$_2$O$_3$F, HCl, H$_2$O): Theoretical: C(56.48) H(5.27) N(7.32); Experimental: C(56.50) H(5.31) N(7.21).

EXAMPLE 9

2-(6-Fluoro-2-methoxy-1,4-benzodioxan-2-yl)-imidazoline Hydrochloride

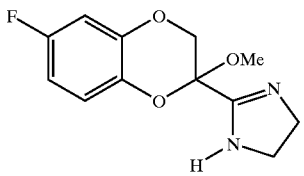

This compound is prepared via 2-(6-fluoro-2-methoxy-1,4-benzodioxan-2-yl)methanol described in J.Med.Chem. (1987), 30, 814, and then converted into the imidazoline according to J.Med.Chem. (1983), 26, 823, or J.Med.Chem. (1985), 28, 1054. Elemental analysis: ($C_{12}H_{13}N_2O_3F$, HCl).

EXAMPLE 10

2-(7-Fluoro-2-methoxy-1,4-benzodioxan-2-yl)-imidazoline Hydrochloride

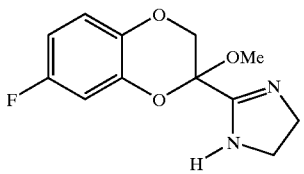

This compound is prepared via 2-(7-fluoro-2-methoxy-1,4-benzodioxan-2-yl)methanol described in J.Med.Chem. (1987), 30, 814, and then converted into the imidazoline according to J.Med.Chem. (1983), 26, 823, or J.Med.Chem. (1985), 28, 1054. Elemental analysis: ($C_{12}H_{13}N_2O_3F$, HCl).

EXAMPLE 11

2-(8-Fluoro-2-methoxy-1,4-benzodioxan-2-yl)-imidazoline Hydrochloride

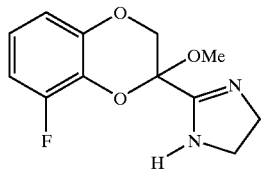

Stage 1: 5/8-Fluoro-1,4-benzodioxane-2-carbonitrile:

15.8 ml of trifluoroacetic anhydride (23.4 g, 0.11 mol) are added dropwise to a solution containing 20 g of 5/8-fluorobenzodioxane-2-carboxamide, obtained in Stage 1 of Example 1, and 16.4 ml of pyridine (16.1 g, 0.2 mol) in 20 ml of dioxane maintained at 0° C. in an ice bath. The reaction is kept cold for 2 hours and is then extracted with $Et_2O$/1N HCl. The acidic phase is washed 3 times with ether. The ether phases are dried over $MgSO_4$, filtered and then evaporated to dryness. 16.34 g of a crude mixture are obtained, and are re-used in the following step without further purification.

Stage 2: 2-Bromo-8-fluoro-1,4-benzodioxane-2-carbonitrile:

A solution containing 16.34 g of 5/8-fluoro-1,4-benzodioxane-2-carbonitrile (91.3 mmol), 17.87 g of N-bromosuccinimide (100 mmol) and 200 mg of benzoyl peroxide in 500 ml of carbon tetrachloride is refluxed for 5 days. The reaction mixture is cooled to room temperature and the succinimide precipitate is then removed by filtration. The filtrate is evaporated to dryness to give 22.2 g of a crude mixture containing 2-bromo-5-fluoro-1,4-benzodioxane-2-carbonitrile and 2-bromo-8-fluoro-1,4-benzodioxane-2-carbonitrile. The two isomers are separated by flash chromatography on a column of silica (99.5/0.5 petroleum ether/ethyl acetate). 7 g of 2-bromo-5-fluoro-1,4-benzodioxane-2-carbonitrile and 6.2 g of the desired 2-bromo-8-fluoro-1,4-benzodioxane-2-carbonitrile are obtained.

2-Bromo-8-fluoro-1,4-benzodioxane-2-carbonitrile:

$^1$H NMR (400 MHz, $CDCl_3$): 7.02 (m, 1H, aromatic ); 6.83 (m, 2H, aromatics ); 4.58 (d, J=11.6 Hz, 1H, H3A ); 4.48 (d, J=11.6 Hz, 1H, H3B).

Stage 3: 2-(8-Fluoro-2-methoxy-1,4-benzodioxan-2-yl)-imidazoline

A solution containing 1.6 g of 2-bromo-8-fluoro-1,4-benzodioxane-2-carbonitrile (6.2 mmol) and 40 mg of sodium methoxide (0.7 mmol; 0.12 mol. eq.) in 50 ml of methanol are stirred at room temperature for ¾ hour. 0.456 ml of ethylenediamine (0.41 g; 6.8 mmol; 1.1 mol. eq.) is then added, followed by 2.3 ml of a 3N HCl/iPrOH solution (6.8 mmol; 1.1 mol. eq.). The reaction mixture is stirred at room temperature for 16 hours and then taken up in a 1N NaOH/$CH_2Cl_2$ mixture. The organic phase is dried over $MgSO_4$, filtered and then evaporated to dryness. The crude product is purified by chromatography on silica under pressure (96/4 $CH_2Cl_2$/MeOH). 0.75 g of pure product is obtained (48% yield).

$^1$H NMR (400 MHz, $CDCl_3$): 6.85 (m, 1H, aromatic); 6.73(m, 2H, aromatics); 4.57 (d, J=11.6 Hz, 1H, H3A); 4.00 (d, J=11.6 Hz, 1H, H3B); 3.76 (broad multiplet, 4H, imidazoline); 3.42 (s, 3H, $OCH_3$).

$^{13}$C NMR (100.03 Hz, $CDCl_3$): 162.34 (C quat. imidazoline), 151.99 (d, J=244 Hz, C8), 144.31 (C4a), 128.90 (d, J=14 Hz, C8a), 121.23 (d, J=9 Hz, C6), 112.51 (d, J=3.7 Hz, C5), 108.79 (d, J=18 Hz, C7), 94.15 (C2), 67.93 (C3), 51.58 ($OCH_3$), 50.5 (very broad multiplet, $CH_2$ imidazoline).

The hydrochloride is obtained by dissolving the base in ether and then adding one equivalent of a 3N HCl/iPrOH solution. The solid formed is filtered off, washed with ether and then dried under vacuum.

Elemental analysis: Theoretical C(49.92) H(4.89) N(9.70);

Experimental: C(49.63) H(4.93) N(9.54).

The bases enantiomers are separated by chiral HPLC (Chiralpack AD column; 90/10/0.1 hexane/iPrOH/diethylamine; 100 ml/min; 254 nm).

The hydrochlorides are obtained by dissolving the base in ether and then adding the equivalent of a 3N HCl/iPrOH solution. The solid formed is filtered off, washed with ether and then dried under vacuum.

(+) enantiomer:

$[\alpha_D]^{25}$ (c=0.253; MeOH)=+86.2°.

Melting point=262° C.

Elemental analysis ($C_{13}H_{15}N_2O_3F_1$, HCl):

Theoretical: C(49.92) H(4.89) N(9.70);

Experimental: C(49.70) H(4.87) N(9.56).

(−) enantiomer:

$[\alpha_D]^{25}$ (c=0.429; MeOH)=−85.8°.

Melting point =260° C.

Elemental analysis ($C_{13}H_{15}N_2O_3F_1$, HCl):

Theoretical: C(49.92) H(4.89) N(9.70);
Experimental: C(49.55) H(4.83) N(9.57).

The invention also covers the use of the compounds of formula 1 for the preparation of a medicinal product such as an .₂-adrenergic receptor antagonist used and intended in this respect to treat neurodegenerative diseases and their progression, cognitive and memory disorders, and also attention deficit and vigilance deficit, Alzheimer's disease, Parkinson's disease, Huntington's chorea, amyotrophic lateral sclerosis, Creutzfeld-Jacob disease, progressive supranuclear paralysis, and also the evolution of these diseases or disorders. Cerebral attacks, ischemic and post-ischemic cerebral disorders, depression, narcolepsy and male sexual dysfunctions are also concerned, as are disorders associated with acquired immunodeficiency syndrome. Finally, pathologies relating to cerebral attacks, to ischemic disorders, to cerebrovascular accidents and their consequences, and also to depression, narcolepsy, male sexual dysfunctions, disorders associated with acquired immunodeficiency syndrome, and also the evolution of these diseases or disorders, are concerned.

What is claimed is:

1. A compound corresponding to the structure of general formula 1:

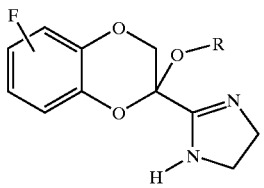

Formula 1 in which:
R represents a linear, branched or cyclized alkyl or alkenyl group containing 1 to 7 carbon atoms, or a benzyl group, and
the fluorine atom can occupy position 5, 6, 7 or 8, in their racemic form and their dextrorotatory and levorotatory pure enantiomeric forms, and also the addition salts thereof.

2. The compound of formula 1 as claimed in claim 1, characterized in that the radical R is a methyl group.

3. The compound of formula 1 as claimed in claim 1, characterized in that the radical R is an ethyl group.

4. The compound of formula 1 as claimed in claim 1, characterized in that the radical R is an n-propyl group.

5. The compound of formula 1 as claimed in claim 1, characterized in that the radical R is a isopropyl group.

6. The compound of formula 1 as claimed in claim 1, characterized in that the radical R is an isobutyl group.

7. The compound of formula 1 as claimed in claim 1, characterized in that the radical R is a cyclopropylmethyl group.

8. The compound of formula 1 as claimed in claim 1, characterized in that the radical R is a allyl group.

9. The compound of formula 1 as claimed in claim 1, characterized in that the radical R is a benzyl group.

10. The compound as claimed in claim 1, characterized in that the fluorine atom occupies position 5.

11. A process for preparing the compounds of formula 1 as claimed in claim 1, characterized in that 3-fluorocatechol is reacted with 2,3-dibromo-propionamide, and the 5-fluorobenzodioxane-2-carboxamide derivative obtained is crystallized, and is then dehydrated into nitrile, and then brominated with NBS, subjected to a treatment with a sodium alkoxide to form the intermediate imidate, which is then treated with ethylenediamine in an alcohol.

12. A process for preparing the compounds of formula 1 as claimed in claim 1, characterized in that 6- or 7-fluoro-2,3-dihydro-benzo[1,4]dioxin-2-yl)methanol is converted into nitrile, and this nitrile is treated according to the process of claim 11.

13. A pharmaceutical composition, characterized in that it comprises at least one compound of formula 1 as claimed in claim 1, and a suitable excipient.

14. A method of treating a person having a neurodegenerative disease, comprising: administering the compound of formula 1 as recited in claim 1 to the person.

15. A method of treating a person having a disorder selected from one or more of cognitive disorders, memory disorders, attention deficit disorders and vigilance deficit disorders; comprising: administering the compound of formula 1 as recited in claim 1 to the person.

16. A method of treating a person having Alzheimer's disease, comprising: administering the compound of formula 1 as recited in claim 1 to the person.

17. A method of treating a person having a disorder selected from one or more of Parkinson's disease, Huntington's chorea, amyotrophic lateral sclerosis, Creutzfeld-Jacob disease, and progressive supranuclear paralysis; comprising: administering the compound of formula 1 as recited in claim 1 to the person.

18. A method of treating a person having a pathology selected from cerebral attacks, ischemic disorders, cerebrovascular accidents and their consequences, depression, narcolepsy, male sexual dysfunctions, and disorders associated with acquired immunodeficiency syndrome; comprising: administering the compound of formula 1 as recited in claim 1 to the person.

19. A method of treating an animal having a neurodegenerative disease, comprising: administering the compound of formula 1 as recited in claim 1 to the animal.

* * * * *